United States Patent
Aliberti et al.

(10) Patent No.: US 10,663,655 B2
(45) Date of Patent: May 26, 2020

(54) OPTICAL FIBER AND DEVICE FOR RELEASING MOLECULES

(71) Applicants: Anna Aliberti, Siano (IT); Andrea Cusano, Caserta (IT); Antonello Cutolo, Naples (IT); Menotti Ruvo, San Nicola la Strada (IT)

(72) Inventors: Anna Aliberti, Siano (IT); Andrea Cusano, Caserta (IT); Antonello Cutolo, Naples (IT); Menotti Ruvo, San Nicola la Strada (IT)

(73) Assignee: CENTRO REGIONALE INFORMATION E COMMUNICATION TECHNOLOGY—CERICT S.C.R.L., Benevento (IT)

( * ) Notice: Subject to any disclaimer, the term of this patent is extended or adjusted under 35 U.S.C. 154(b) by 0 days.

(21) Appl. No.: 16/098,344

(22) PCT Filed: May 2, 2017

(86) PCT No.: PCT/IB2017/052533
§ 371 (c)(1),
(2) Date: Nov. 1, 2018

(87) PCT Pub. No.: WO2017/191552
PCT Pub. Date: Nov. 9, 2017

(65) Prior Publication Data
US 2019/0146149 A1 May 16, 2019

(30) Foreign Application Priority Data
Feb. 5, 2016 (IT) .................. 102016000043206

(51) Int. Cl.
*G02B 6/02* (2006.01)
*A61K 41/00* (2020.01)
(Continued)

(52) U.S. Cl.
CPC ...... *G02B 6/02333* (2013.01); *A61K 41/0042* (2013.01); *A61K 47/50* (2017.08); *A61K 47/6957* (2017.08); *A61M 37/00* (2013.01)

(58) Field of Classification Search
None
See application file for complete search history.

(56) References Cited

U.S. PATENT DOCUMENTS 5,094,819 A * 3/1992 Yager ................. G01N 21/6428
250/227.14

FOREIGN PATENT DOCUMENTS

WO   1996/023543 A1   8/1996

OTHER PUBLICATIONS

International Search Report and Written Opinion for corresponding Application No. PCT/IB2017/052533 (dated Aug. 4, 2017).
(Continued)

*Primary Examiner* — Chad H Smith
(74) *Attorney, Agent, or Firm* — Pepper Hamilton LLP

(57) ABSTRACT

The present invention relates to an optical fiber and a device including the optical fiber. The optical fiber is an optical fiber (1) functionalized with at least one particle (1) of a polymeric gel comprising at least one photosensitive molecule (7) and at least one biomolecule (6), wherein the at least one particle (2) of the polymeric gel is covalently bound to said optical fiber (1).

12 Claims, 2 Drawing Sheets

(51) Int. Cl.
  *A61K 47/69*  (2017.01)
  *A61K 47/50*  (2017.01)
  *A61M 37/00*  (2006.01)

(56) References Cited

OTHER PUBLICATIONS

Zamadar et al., "Photosensitizer Drug Delivery via an Optical Fiber," J. Am. Chem. Soc. 133(20):7882-7891 (2011).
Kim et al., "A Fiber-Optic UV Sensor Based on a Side-Polished Single Mode Fiber Covered with Azobenzene Dye-Doped Polycarbonate," Sensors and Actuators A: Physical 160(1-2):19-21 (2010).
Bartusik et al., "Fluorine End-Capped Optical Fibers for Photosensitizer Release and Singlet Oxygen Production," J. Org. Chem. 77(10):4557-4565 (2012).
Mahendran et al., "A Hand-Held Fiber-Optic Implement for the Site-Specific Delivery of Photosensitizer and Singlet Oxygen," Photochem. Photobiol. 87(6):1330-1337 (2011).

\* cited by examiner

OPTICAL FIBER AND DEVICE FOR RELEASING MOLECULES

This application is a national stage application under 35 U.S.C. § 371 of PCT Application No. PCT/IB2017/052533, filed 2 May 2017, which claims priority of Italy Application No. 102016000043206, filed 2 May 2016, which are hereby incorporated by reference in their entirety.

FIELD OF THE INVENTION

The present invention relates to an optical fiber and a device for releasing molecules.

DESCRIPTION OF THE PRIOR ART

One of the supporting and complementary strategies for molecular medicine approaches involves the use of drug delivery systems. Typically, such systems provide that a natural or synthetic species, called carrier, is combined with a drug or an active agent, so that this latter is transported into the diseased tissue and released in a controlled manner. Release can take place through a continuous or pulsed mechanism. In particular, in the second case, the drug is released due to specific stimuli of chemical or physical nature, such as a pH variation. A controlled release system allows administration of lower doses of drug and a reduction in frequency of administration, thus a better compliance by the patient. Having a delivery system can prove to be very beneficial in drug administration to cope with pharmacokinetic and pharmacodynamic problems, such as low bioavailability and lack of selectivity.

However, known drug delivery systems involve a number of disadvantages. In particular, the level of selectivity and specificity of known drug delivery systems is not satisfactory. Indeed, specific tissue or human compartments that require the administration of one or more active ingredients are very difficult to reach with the known systems.

Furthermore, known carriers also exhibit a number of disadvantages linked to the possible toxicity or non-biocompatibility of the constituent material, to the formation of unwanted compounds due to carrier degradation, or to non-specific accumulation in healthy cells or tissues, thus altering the functionality of host organs.

The object of the present invention is therefore to provide a system for releasing molecules that do not exhibit the disadvantages of prior art.

SUMMARY OF THE INVENTION

The inventors have surprisingly found that they could functionalize an optical fiber with particles of a polymeric gel comprising a photosensitive molecule and a molecule of interest, which could be released to the site concerned if illuminated with a light beam that was designed to ensure that the polymeric gel releases the biomolecule comprised in it.

Therefore, the invention relates to an optical fiber 1 functionalized with at least one particle 2 of a polymeric gel comprising at least one photosensitive molecule 7 and at least one biomolecule 6, wherein the at least one particle 2 is covalently bound to the optical fiber 1.

in the present invention, when using the term:
"photosensitive molecule" it is meant a molecule or a particle capable of being excited by a light source and giving rise to chemical reactions that cleave chemical bonds, to conformational changes and energy transfers. With photosensitive molecules we also mean molecules that generate a photothermal effect; when we refer to a particle as a photosensitive molecule, we mean a particle of any shape and size.

"biomolecule" it is meant a molecule for therapeutic or diagnostic use to be released to a site of interest.

Therefore, according to the invention, when at least one polymeric gel particle 2 is irradiated by a beam of light, the at least one biomolecule is capable to be released by the at least one particle 2 and transported into a human or animal tissue or compartment.

Specifically, the optical fiber 1 can be connected to a lighting system 4 configured to generate a light beam that propagates from inside the optical fiber to the outside, wherein the optical fiber 1 is functionalized with at least one particle 2 of a polymeric gel comprising at least one photosensitive molecule 7 and at least one biomolecule 6, wherein the at least one particle 2 is covalently bound to at least one outer surface 1a, 1b of the optical fiber 1. When the at least one particle 2 is irradiated by the beam of light, the at least one biomolecule can be released from the particles 2 and delivered to a human or animal tissue or compartment.

According to another aspect, the invention relates to a device 8 for releasing at least one biomolecule in a human or animal tissue or compartment, the device 8 comprising:
at least one optical fiber 1 according to the invention, wherein said photosensitive molecule 7 is adapted to be activated in a predetermined range of wavelengths;
a lighting system 5 configured to generate a light beam that propagates from inside the optical fiber to the outside, wherein said light beam has a wavelength comprised in said predetermined wavelengths range,
an optical connector 3 that connects the optical fiber to the lighting system 5.

Therefore, the invention provides advantageously to incorporate carrier-based drug delivery systems with an optical fiber that acts as a remote controllable probe to activate the release of one or more active principles. In other words, the invention provides an optical fiber functionalized with a drug delivery system capable of delivering the active principles in specific compartments or tissues in the patient's body.

According to the invention, the polymeric gel, which is a drug delivery system, is covalently bound to the optical fiber.

The invention thus relates to a system for the administration of active principles (biomolecules) with an optical fiber advantageously having a beneficial therapeutic efficacy.

DETAILED DESCRIPTION OF THE INVENTION

Figure 1:
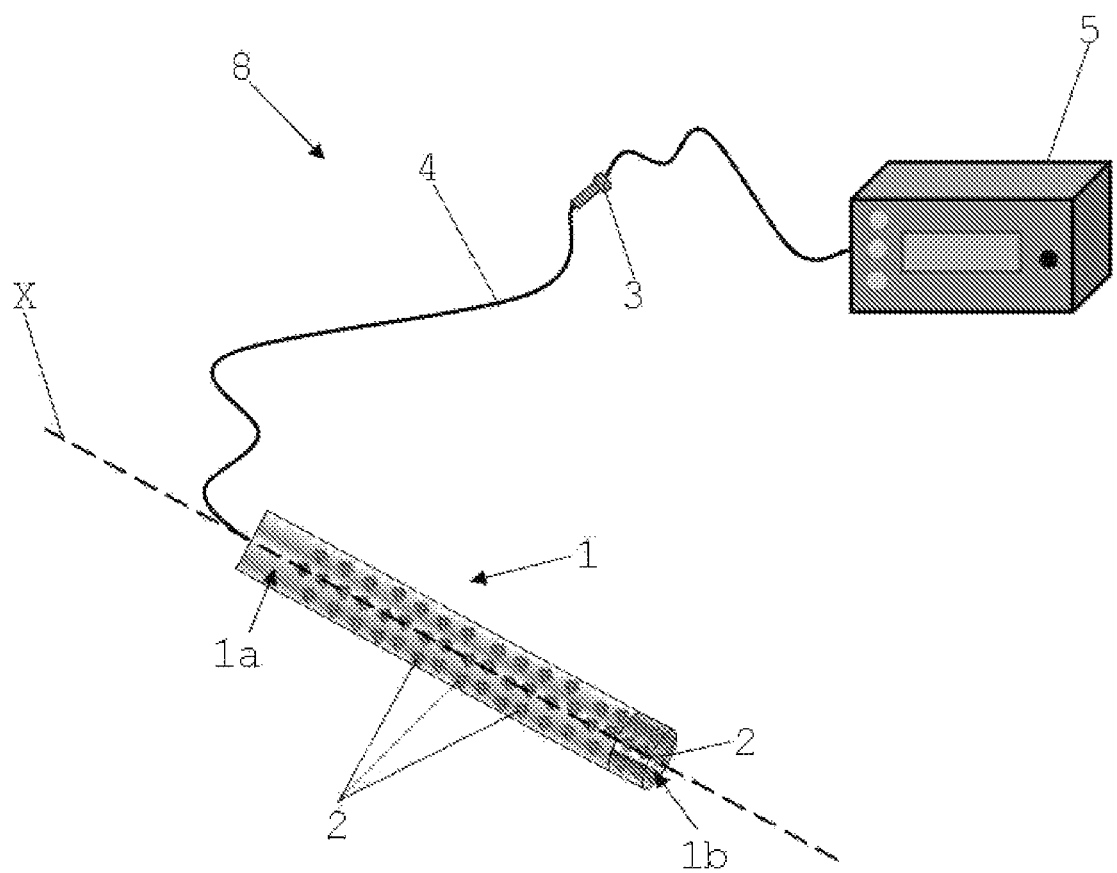
FIG. 1 illustrates a schematic view of an optical fiber bound to the polymeric gel and a device comprising the optical fiber according to the invention.

The invention relates to an optical fiber functionalized with at least one particle 2 of a polymeric gel comprising at least one photosensitive molecule 7 and at least one biomolecule 6, wherein the at least one particle 2 is covalently bound to the optical fiber 1.

Preferably; according to the invention, the optical fiber 1 comprises a very thin, transparent, flexible cylindrical glass element, which is used as a guide for light beams, also known as light guide. Since the optical fiber diameter can be reduced up to a micron, which is to the order of magnitude of the wavelength of the light radiation, optical fibers act as waveguides for electromagnetic waves in visible or near infrared range. Optical fibers also have excellent versatility and high flexibility and can be easily integrated into any circuit or device.

Advantageously, since the fiber is thin and flexible, it can be easily and tightly folded. According to the invention, insertion of a fiber into the body requires only a small incision or cut and the release of biomolecules can be concentrated on the target without damaging the surrounding tissue. Therefore, an optical fiber allows minimally invasive medical procedures and consequently its use implies less traumatic experiences for patients.

The invention contemplates releasing one or more therapeutic molecules (biomolecules) contained in at least one particle of a polymeric gel indicated by reference 2, preferably a microgel and/or nanogel, and covalently bound to the optical fiber, preferably to at least one outer surface 1a, 1b of the optical fiber 1. Microgel and nanogel are respectively formed by at least one particle having micrometric and/or nanometric sizes. In the present invention, with the term nanogels it is meant preferably polymeric gel particles having a hydrodynamic radius with a variable size in the range of 0.010 to 0.050 μm, whereas the term microgels refers to hydrogel particles with a hydrodynamic radius of variable size in the range of 0.1 to 2.5 μm.

The at least one particle of polymeric gel is covalently bound, preferably to the outer surface of the optical fiber.

At least one polymeric gel particle is bound to the optical fiber by the formation of a covalent bond between functional groups present on the optical fiber and complementary functional groups present on the surface of the particles. The type of covalent bond preferably occurs on at least part of the optical fiber surface and, more preferably, it may be an amide bond, an ester, ether and thioether bond, a carbon-carbon, a carbon-nitrogen, a carbon-sulphur, a carbon-phosphorus, a carbon-oxygen, a carbon-silicon bond.

The optical fiber 1 of the invention can be functionalized with at least one particle of a first polymeric gel and with at least one particle of other polymeric gels.

The invention thus provides an optical fiber for controlled release of one or more biomolecules in vitro and/or in vivo mediated by a polymeric gel, preferably a nano/micro carrier made of a polymeric gel, such as nanogels or microgels. Preferably, the polymeric gel is bound to the end, or tip, of the optical fiber and/or the outer lateral surface, or cladding, of the optical fiber. In particular, with the term "tip" it is meant the end surface which is transverse to the longitudinal axis of the fiber and with the term "cladding" it is meant the lateral surface of the fiber parallel to the longitudinal axis of the fiber itself.

Figure 2:
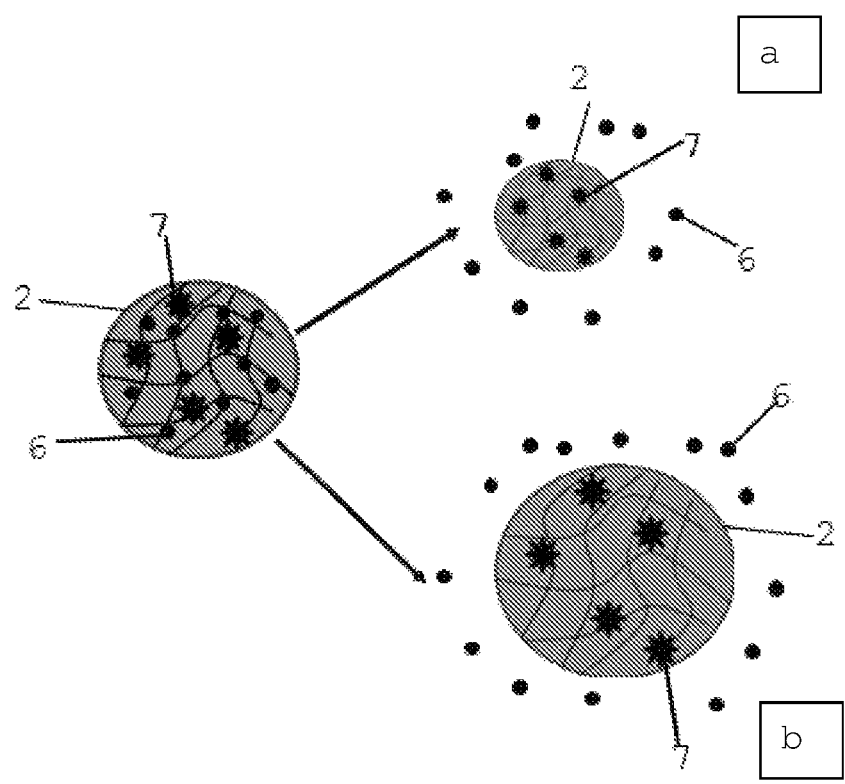
FIG. 2 shows schematically a detail of the polymeric gel according to the invention and two alternative biomolecule release mechanisms respectively indicated by 2a (compression of the polymeric gel and ejection of the biomolecule) and 2b (molecular mesh opening and release of the molecule).

Release of the at least one biomolecule 6 is implemented and, preferably, modulated by light passing through the optical fiber and is based on the interaction of one or more photosensitive molecules 7, such as fluorophores, particles, small, photosensitive organic molecules bound within the three-dimensional structure of the at least one polymeric gel particle (FIG. 2).

The biomolecule 6 to be released is therefore contained in the polymeric gel and is maintained therein by physical or chemical interactions during the preparation phase thereof. According to the invention, the interaction between light and at least one photosensitive molecule 7 induces photothermic heating effects of the gel, followed by compression processes of the polymeric gel (decrease in size) and ejection (thus release) of the biomolecule 6 trapped therein (FIG. 2a).

Alternatively, the interaction between light and photosensitive molecules can also result in the cleavage of chemical bonds or cis-trans isomerization phenomena. These phenomena lead to changes in the three-dimensional chemical structure, which induce an opening of the microgel molecular mesh and hence in a modulation controlled by the release light of the biomolecules contained within the polymer network (FIG. 2b).

The optical fiber 1 is therefore covalently bound to at least one (micro and/or nanogel) polymer particle, preferably on the tip and/or cladding of the fiber, depending on different configurations. Long Period Grating (LPG) fibers or photonic crystal fibers (known as Photonic Crystal Fibers-PCF from Anglo-Saxon terminology) also allow for lateral surface functionalization: in such configuration, the number of polymeric gel particles can be increased on the basis of the surface extension, and, consequently, also the amount of biomolecule released after irradiation can be increased.

Advantageously, the other end of the optical fiber, opposed to the tip, can be connected to a device that allows illumination of the optical fiber. This type of lighting device is well known in the relevant field and will therefore not be described in detail.

The invention allows a reduction of the non-specific tissue damage caused by common systemic therapies. In particular, the invention allows a non-invasive treatment mode and one or more therapeutic molecules can be physically directed, via an optical fiber, to the target area, and the light used to energize the photosensitive molecule can be accurately directed through the use of the optical fiber (FIG. 1). Advantageously, the invention provides an optical fiber capable of assisting and guiding the controlled release of biomolecules within human or animal tissues and compartments, particularly for locoregional therapies.

The optical fiber 1 can have preferably a diameter in the range of 80 to 800 μm. It can be made of plastic or glassy material and the light can propagate within it in a guided manner and with different powers. The optical fiber is very flexible and resistant to electrical disturbances and temperature variations. It allows a transmission of the light and radiation of the polymeric gel (nano and/or micrometric size), which is placed near the target area by means of the optical fiber and is physically modified or more generally "activated" by light pulse thus delivering activated molecules in a pulsated way or on command. Spatial proximity to the target area facilitates local absorption of active biomolecules by making their action more specific and therefore potentially less toxic.

In one embodiment of the invention, the active molecule is chemically bound to a molecular recognition probe for overexpressed receptors in target cells or tissues, in order to further increase the selectivity of the bioactive molecule for target cells or sites.

In another aspect, the invention relates to a device 8 for releasing at least one biomolecule in a human or animal tissue or compartment, the device 8 comprising:
at least one optical fiber 1 according to the invention, wherein said photosensitive molecule 7 is adapted to be activated in a predetermined range of wavelengths;

a lighting system 5 configured to generate a light beam that propagates from inside the optical fiber to the outside, wherein said light beam has a wavelength comprised in said predetermined wavelengths range;

an optical connector 3 that connects the optical fiber to the lighting system 5.

The optical connector is preferably connected to the optical fiber 1 and to the lighting system 5 by means of a patchcord (or optical braces) 4 or by means of a pre-connected optical cable.

The lighting system 5 generates a light beam according to the invention at a given wavelength range, which is capable of exciting at least one photosensitive molecule.

Preferably, said predetermined wavelength range is in the range of 200 nm to 1700 nm, more preferably 300 to 500 nm or more preferably 600 to 850 nm.

The device of the invention is schematically represented in FIG. 1, in which the optical fiber 1 can be connected to a lighting system 5 configured to generate a light beam that propagates from inside the optical fiber to the outside, wherein the optical fiber 1 is functionalized with at least one particle 2 of a polymeric gel comprising at least one photosensitive molecule 7 and at least one biomolecule 6, wherein the at least one particle 2 is covalently bound to at least one outer surface 1a, 1b of the optical fiber 1. When the at least one particle 2 is irradiated by the light beam, the at least one biomolecule can be released from the particles 2 and delivered to a human or animal tissue or compartment.

The fiber and the device of the invention provide controlled release of at least one biomolecule 6.

Preferably, said at least one biomolecule is selected from the group consisting of growth factors, neuroprotective molecules, molecules active for regeneration of the central nervous system, drugs and prodrugs and combination thereof, antineoplastic agents, biological response modifiers, hormones, vitamins, peptides, enzymes, antiviral agents, radioactive compound, monoclonal antibodies, genetic material, and cells.

Preferably, said biomolecule is preferably an anticancer drug selected from the group consisting of alkylating agents, antimetabolites, antimitotics, anti-tumor antibiotics, and monoclonal antibodies.

Among the antimetabolites alkyl sulfonates (Busulfan), nitrosoureas (Carmustine, Lomustine), nitrogen mustards (Cyclophosphamide, Mechlorethamine, Uramustine, Melphalan, Chlorambucil, Ifosfamide), platinum compounds (Cisplatinum, Carboplatin, Oxaliplatin), hydrazine (Procarbazine), thiazine (Dacarbazine) and aziridine (Thiotepa) can be mentioned.

Among the antimetabolites folic acid analogues (METOTREXATO), purine analogues (Azathioprine, Mercaptopurine, Fludarabine, Thioguanine) and the analogs of pyrimidine (5-fluorouracil, Floxuridine, Cytosine arabinoside) can be mentioned.

Among the antimitotic agents Taxanes (Paclitaxel), Vinca alkaloids (Vincristine, Vinblastine) can be mentioned.

Among anti-tumor antibiotics anthracycline (Doxorubicin), anthracenedion (Mitoxantrone), streptomycin (Actinomycin, Bleomycin, Mitomycin) can be mentioned.

Among monoclonal antibodies Bevacizumab, Cetuximab, Trastuzumab, Denosumab, Rituximab can be mentioned.

Other anticancer agents include molecules that inhibit growth factor or kinase receptors: these include Gefitinib, Imatinib, Sunitinib.

The fiber and device of the invention allow local healing and regenerative therapies, avoiding the use of systemic therapies which may involve the onset of various undesirable side effects.

The optical fiber of the invention is optically connected to a lighting system comprising a light source capable of controlling and radiating with (single band or multiple band and possibly pulsed) light having a wavelength necessary for photo-activation of the biomolecule release.

Advantageously, the device of the invention allows controlled release of drugs in vivo by photo-activation (classic application as an in vivo medical device) and controlled release of drugs in vivo (in animals) or in vitro (in cell cultures), for example, for clinical trial of therapeutic efficacy.

In a further aspect, the invention relates to a process for the production of the optical fiber 1 of the invention, comprising the steps of:

a) synthesizing a particle 2 of a polymeric gel having reactive functional groups, b) preparing a solution comprising said at least one polymeric gel particle 2;

c) treating an optical fiber 1 in such a way that at least one of its outer surfaces (1a, 1b) is provided with reactive functional groups capable of interacting covalently with the functional reactive groups of at least one particle 2 of the polymeric gel, g) immersing the optical fiber in the solution of step b), so that the at least one particle 2 of polymeric gel is covalently bound to said at least one outer surface (1a, 1 b) of the optical fiber.

Therefore, the at least one polymeric gel particle is bound to the optical fiber by formation of a covalent bond between functional groups present on the optical fiber and complementary functional groups present on the surface of the particles. The type of covalent bond can be an amide bond, an ester, ether or thioether bond, a carbon-carbon bond or any other chemical covalent bond that can be hypothesized and produced by a technician skilled in the field.

Preferably, step (a) includes the synthesis of polymeric gel particles by precipitation polymerization or emulsion.

Preferably, said solution is concentrated at 5-10% by weight/volume in step b).

In step c), said treatment is preferably carried out by silanization with silanes carrying second functional reactive groups, preferably epoxides or thiols or amines or carboxylic groups, or through heterofunctionalized cross linkers carrying a thiol at either end or an alkyne or an azide to produce the so-called "click chemistry" reactions.

Methods of Synthesis of the Polymeric Gel

The category of polymeric gels, preferably micro/nanogels, is a type of polymeric material suitable for use as substrates for the release of biomolecules in general. A peculiarity of these systems is their great ability to absorb water, which on the one hand gives them high biocompatibility and on the other modulates the release kinetics of any drugs trapped therein. The polymeric gel of the invention, preferably micro/nanogel, indicated by reference 2, may be considered as a polymer solution having the cohesive properties of a solid and the diffusive transport properties of a liquid.

The present invention preferably provides for the preparation of micro/nanogel particles having a hydrodynamic radius in the range of 0.01 to 5 μm, preferably 0.02 to 5 μm. In the present invention, the term nanogel refers preferably to polymeric gel particles having a hydrodynamic radius with a size variable in the range of 0.010 to 0.050 μm, whereas the term microgels refer to hydrogel particles with a hydrodynamic radius of size variable in the range of 0.1 to 2.5 μm.

Preferably, the hydrodynamic radius is determined by dynamic light scattering. Preferably, but not exclusively, when nanogels are used, their hydrodynamic radius, determined by dynamic light scattering, is in the range of 0.020 μm to 0.040 μm. Instead, the hydrodynamic radius of microgels, determined by dynamic light scattering, is preferably in the range of 0.100 to 2.5 μm. Preferably, but not exclusively, when using microgels their hydrodynamic radius is in the range of 0.100 μm and 1.00 μm.

Different polymerization techniques can be used to prepare the polymeric gel of the invention, preferably micro/nanogel, in the form of particle 2 functionalized with suitable molecules capable of assuring the photosensitivity and encapsulation of biologically active molecules. The polymeric gel particles, preferably micro/nanogel, are covalently bound to the optical fiber 1, which is typically pretreated to allow chemical bonding with the polymeric gel particles.

To obtain polymeric gel particles, preferably microgel or nanogel, with specific properties but of general applicability, various techniques have been used and optimized, such as: polymerization by precipitation, emulsion, and multistep processes even in microfluidic systems.

Preferably, the present invention contemplates the synthesis of polymeric gel particles using one or more monomers for polymerization.

Therefore, according to the invention, the optical fiber 1 comprises a polymeric gel obtained by the polymerization of one or more monomers selected from the group consisting of acrylic monomers, vinyl monomers, stimulus-responsive monomers, and bionert monomers.

Preferably, the acrylic monomers are functionalized with carboxyl and/or amino functional groups, preferably selected from a group consisting of acrylic acid, methacrylic acid, fumaric acid, maleic acid, butylmethylacrylate (nBuMA), dimethylaminoethyl acrylate (DMAEA), acrylamide (AAm), aminoethylmethacrylate (Aema), dimethylaminoethyl (meth) acrylate (DMAEMA), N-(3-aminopropyl) methacrylamide (APMA), or polyethylenimine (PEI). Such monomers may be present in the initial composition in amounts in the range of 5 to 30% by weight with respect to the weight of the initial total composition.

Preferably, said bio-inert monomers are selected from a group consisting of monomers derived from ethylene glycol, preferably polyethylene glycol acrylates, polyethylene glycol methacrylates, polyethylene glycol functionalized with acrylamides, methacrylamide functionalized polyethylene glycol, oligo(ethylene glycol)acrylate (OEGA), oligo(ethylene glycol) methacrylate (OEGMA), oligo(ethylene glycol) diacrylate (OEGDA), N-alkylacrylamide, vinylcaprolactone (VCL), and hydroxy-ethyl methacrylate. Such monomers may be present in the initial composition in amounts in the range of 5 to 30% by weight with respect to the weight of the total initial composition.

Preferred stimulus-responsive monomers are N-isopropyl acrylamide or aminoethyl methacrylate and the likes. Such monomers may be present in the initial composition in amounts in the range of 10 to 90% by weight, preferably in the range of 60 to 80% by weight, with respect to the weight of the total initial composition.

Acrylic monomers can be bi-functionalized (cross linkers), preferably in amounts in the range of 0.5 to 10% by weight with respect to the weight of the initial total composition. Such monomers have two or more vinyl groups suitable for the synthesis of the three-dimensional polymerizable polymer network of the invention. The polymeric gel of the present invention may also be derived from light-sensitive acrylic monomers in the range of 0.5 to 25% by weight with respect to the total weight of the initial composition. Such functionalizations with photosensitive molecules can be carried out during polymerization or subsequently (after the polymeric gel synthesis).

Therefore, the optical fiber according to the invention comprises a polymeric gel which, in turn, comprises a photosensitive molecule (7). This is preferably selected from a group consisting of:
   azobenzene or its derivatives,
   a nitrobenzyl derivative,
   a fluorophore, preferably derived from malachite and carbocyanines, and
   a particle of gold and/or silver
   a high refractive index particle.

Preferably, when the photosensitive molecule 7 is a gold and/or silver particle, it preferably has a radius in the range of 5 to 80 nm.

Preferably, the high refractive index particle is a particle of oxide, such as titanium oxide.

A class of photosensitive molecules is represented by azobenzene and its derivatives. These molecules are subject to cis-trans photoisomerization phenomena, responsible for variation in the molecular mesh of the polymeric gel, and thus able to modulate the release.

A second class of photosensitive molecules is represented by nitrobenzyl derivatives. These molecules are subject to photocleavage phenomena, responsible for the cleavage of chemical bonds in the polymer network, resulting in an increase of the molecular mesh and the release of the biomolecules, (FIG. 2,b).

The polymeric gels of the present invention may also be derivatized with fluorophores, such as malachite and carbocyanine derivatives, in an amount of 0.5 to 25% by weight with respect to the total weight of the initial composition. These photosensitive elements guarantee the release of molecules by a photothermic effect of heating the polymeric gel, narrowing the molecular mesh and the associated expulsion of the trapped biomolecules. (FIG. 2.a)

Particles 2 of the polymeric gel of the invention, preferably microgel or nanogel, can also be derivatized with nanoparticles or nanorods of gold or silver having variable dimensions between 1 and 80 nm. Even such gold nanoparticles give rise to a photothermic effect, heating the microgel, and subsequent expulsion of any molecule loaded inside the three-dimensional mesh of the polymeric gel.

Optical Fiber Functionalization Methods

The optical fiber 1 is made of two parts: the innermost one is the nucleus, or core, which has a higher refractive index, and the outer one is the mantle, or cladding, which has a lower refractive index. The fibers used within the scope of the invention herein described may be classified according to the core and cladding materials.
   Silica-silica or quartz-quartz: also called AS (All Silica), both core and cladding are made of silica; they have the best optical characteristics among the step index fibers, and are therefore able to transmit higher power radiations than other fiber types.
   Silica-plastic: also called PCS (Plastic Cladding Silica), they have a silica core and cladding made of silicone material; they have good optical characteristics and can be used with medium and low power radiations.
   Silica-hard cladding: also called HCS (Hard Cladding Silica), they are like PCSs except for the cladding, made up of a silicone material with strong mechanical characteristics (hard cladding) and better optics.

The fibers can be monomode or multimode. In monomode fibers, the beam within them propagates in one way, almost parallel to the axis of the fiber, because it is forced by the very small radius of the core. Generally, their diameter is in the order of a few microns. Multimode fibers have larger dimensions than the previous ones (200 to 800 microns in diameter) and can be stepped (step index) or graded (graded-indes) depending on whether the refractive index is constant throughout the core, decreasing sharply in the cladding, or decreasing gradually from the center of the core up to the separation region between core and cladding.

Alternatively, the use of the so-called "photonic crystal fibers (Photonic Crystal Fibers—PCF), or microstructured fibers, is envisaged. PCFs are obtained by making a non-necessarily periodic grating of air holes all along their length in the silica. These structures allow the light to be confined by total modified reflection or due to introduction of a photonic band-gap that characterizes the periodic grating of air holes on the cross-section of the fiber. These new structures have unusual propagation characteristics and fundamental optical gap band effects, which allow it to be used for many applications, also because the micro tubes can be filled with liquids or other substances to give a multitude of effects.

Also optical fibers, endowed with core and cladding, are used on a length of which at least one Long Period Grating (LPG) has been inscribed. One or more thin polymer layers are deposited on the optical fiber cladding. Said layer of materials is deposited along the fiber portion where the gratings are present and at least one layer, adjacent to the cladding, has a refractive index higher than said cladding. The thickness of said layer of materials is selected so as to adjust the operating regime of the device.

In LPGs, coupling occurs between the fundamental mode (propagating in the core) and discrete modes (co-propagating in the cladding) by means of reflection to the cladding-outer medium interface. Interaction between modes creates a series of spectrum attenuation bands, each of which is centered at a discrete wavelength corresponding to the coupling of the guided fundamental mode (in the nucleus) with different co-propagating modes (in the mantle) and which are strongly attenuated.

The optical fiber functionalization process depends on the type of surface in question. In the case where the surface of the optical fiber, i.e. the tip 1b and/or the cladding 1a, is made of silica, silanization protocols are optimized with silanes bearing reactive chemical groups, such as epoxides, thiols, amines or carboxylic groups for the subsequent anchoring of microgels functionalized in a complementary way.

In the case of gold-bearing fibers, the self-assembled monolayer approach is used as a functionalization protocol, which involves the use of heterofunctionalized cross linkers with a thiol at one end.

Polymeric Gel Particles to Optical Fiber Bonding Methods

The particles can be bound to the tip of the optical fiber and/or along the surface of the cladding depending on the selected fiber configuration. The functionalization of the surface of the above-described microgels is obtained during the synthesis, by addition of acrylate monomers with functional groups on the side chain (e.g. carboxylic groups, amines or hydroxyls, as described in Example 1). Other groups, useful for chemoselective ligation or green chemistry, may be added as protected or unprotected acrylate monomers, so as to address particular issues related to the anchoring phase on the surface. The conjugation reactions of each of the above mentioned functional groups are carried out in aqueous or organic solutions also by means of pre-activated crosslinkers.

Methods and Mechanisms for Releasing Biomolecules

The crosslinked structure of polymeric gels, preferably nano/micro gels, is liable to absorb/release high amounts of solution by means of diffusion (hydrogel swelling/deswelling). The amount of diffused solution depends on the number and average size of the molecular mesh and how such mesh is interconnected (FIG. 2).

The characteristics of swelling and diffusion of the hydrogel in solution are influenced by the following factors: chemical-physical composition of the swelling solution (pH, ionic strength, molecular concentration, etc,); polymer composition (presence of hydrophilic and hydrophobic groups); temperature.

Any biologically active molecule or molecule mix and/or drug may be loaded into the polymeric gel particles, preferably microgel or nanogel. Loading of the molecules may take place after the synthesis of the polymeric gels, so that, to ensure biocompatibility, residual starting and/or initiator material within the polymeric gel (microgel/nanogel) can be completely removed by washing.

The main mechanism regulating the controlled release of the active principle is triggered by the passage of light through the fiber.

Absorption of light within the polymeric matrix of the gel can result in a compression of the microgel size or an opening of the molecular mesh by splitting or reorganizing the polymer chain.

The diffusion rate of the active principle depends on the degree of matrix crosslinking. Release of the molecules may also be influenced by the swelling rate of the polymer matrix depending on both the resistance that he polymer provides against volume increase, and the affinity that the solute exhibit to the matrix (ionic and/or hydrophobic interactions) and the swelling means.

Optoelectronic Set Up

The optoelectronic system has the function of managing both optical fibers and their lighting systems (i.e. light sources) able to modulate in real time the light signal and the relative power supplied by the fibers.

The optoelectronic set-up comprises a lighting system 5 comprising: a power supply and single and/or multiple LED sources. Illumination sources according to the invention may be either narrow or wide band, continuous, or pulsed.

Each of these sources has different spectrum centered at different baricentric wavelengths and can also work in pulsed mode, so that the release can be controlled and modulated in time by light impulses.

Preferably, the optoelectronic set up also includes an optical connector 3 that connects the optical fiber to the lighting system 5.

Preferably, the optoelectronic set up also includes a patch-cord (or optic brace) 4, i.e. a pre-connectorized optical cable.

LED sources, centered at different wavelengths, are powered by power supplies.

The invention will be described with reference to some examplary embodiments of the invention.

Example 1

Synthesis of Microgel Particles by Precipitation-Polymerization

The microgel synthesis by precipitation-polymerization was carried out using an aqueous solution (100 mL) containing a monomeric mixture at 90% by weight/volume of N-isopropyl acrylamide (NIPAM), 5% by weight of acrylic acid (alternatively 3% by weight of hydroxyethylmethacrylate) and 5% by weight of ethylene dimethacrylate (with respect to the total weight of the initial composition). The mixture was then degassed with nitrogen and heated to 70° C. Ammonium persulphate (1% by weight) was added as initiator and the mixture was left under stirring at 70° C. for 4 hours. The microgel particles thus obtained were purified by the excess of unreacted monomers by dialysis (cut off membrane: 10000-14000 Dalton). The hydrodynamic radius of the microgel particles was determined by dynamic light scattering in different buffers (hydrodynamic radius equal to 400 nm in buffer at pH 3, hydrodynamic radius equal to 600 nm in buffer at pH 7.5). Functional groups on the surface of the particles were quantitatively determined by direct and indirect methods, which are known to those skilled in the art as potentiometric titrations, electrophoretic mobility and specific colorimetric assays for functional groups.

Example 2

Conjugation of the Fluorophore Malachite Green-Isothiocyanate to Microgels

The solution of microgel particles prepared in Example 1 was lyophilized, then rehydrated in bicarbonate buffer at pH 9.8. Variable quantities of malachite green-isothiocyanate (in a stoichiometric ratio of 0.01 to 1 and with hydroxyethylamino methacrylate amino groups present therein) were added to the microgel-containing solution. Samples were allowed to react for 12 hours at 4° C. Subsequently, they were purified by dialysis at 4° C. in the dark for three weeks to remove excess reagents (cut off dialysis membrane: 10000-14000 Dalton). After dialysis, the microgels were freeze-dried and then rehydrated in deionized water. The absorption spectra of malachite green isothiocyanate in solution and conjugated to the microgels were acquired by spectrophotometric measurements (data not shown).

Example 3

Synthesis of Microgels Containing Azobenzene
a) Synthesis of 4,4'-Di(Methacrylamide)-Azobenzene Cross Linker Diisopropylethylamine and 4-dimethylaminopyridine were added to a solution of 4,4'-diamino-diazobenzene (4% by weight) in dichloromethane. The solution was cooled to 0° C. and methacryloyl chloride was added by a syringe. The reaction mixture was heated at room temperature and left under stirring for 24 hours. The precipitate obtained was filtered, washed with water and then with methanol. The reaction product was purified by flash chromatography using silica with hexane as eluent. The solid was dried overnight in a vacuum oven at room temperature.

b) Synthesis of Microgels Containing 4,4'-Di(Methacrylamide)-Azobenzene

For the synthesis of microgels containing (methacrylamide)-azobenzene the following monomeric mixture was prepared, consisting of 85% N-isopropylacrylamide (NIPAM) with 5% by weight of 4,4'-di(methacrylamide)-azobenzene as a crosslinker. The NIPAM monomer and the crosslinker were dissolved in deionized water and left under magnetic stirring. The mixture was degassed and the reaction flask filled with nitrogen. The reaction mixture was heated to 70° C. and the reaction started by adding an aqueous solution of ammonium persulfate (1% by weight).

The reaction mixture was allowed to react for 4 hours. Following completion of the reaction, the mixture was filtered through glass wool to remove large aggregates. The obtained microgels were rinsed with deionized water and purified by dialysis (cut off dialysis membrane: 10000-14000 Dalton) to remove the excess reagents and finally lyophilized. The hydrodynamic radius of the microgels thus prepared was determined by dynamic light scattering (hydrodynamic radius equal to 400 nm for pH 7).

Example 4

Synthesis of Microgels Containing Au-Nanorods
a) Synthesis of Gold Nanorods (AuNRs)

The synthesis of AuNRs involved the use of a protocol known as the "seed-mediated growth method".

The procedure consists in preparing nucleation "seeds" by reducing a small amount of tetrachloroauric acid ($HAuCl_4$, 0.12 mL, 5 mM) in aqueous solution and in the presence of a hexadecyltrimethylammonium surfactant (CTAB, 2.5 mL, 0.2M) with a strong reducing agent, such as sodium borohydride ($NaBH_4$, 0.5 mL, 10 mM).

A small amount of these "seeds" (1 ml) is then introduced into the actual growth solution containing 25 ml of a 0.2 M solution of CTAB and 25 ml of a 0.2 M solution of benzyl dimethyl hexadecyl ammonium chloride. 5 mL of an aqueous solution of $HAuCl_4$ (5 mM), silver nitrate ($AgNO_3$, 2.8 mL, 4 mM) and 40 mL of water are added to this solution. After adding 1 ml of an aqueous solution of 0.8 M ascorbic acid, the dark yellow solution becomes colorless.

NRs are purified by three centrifugation cycles at 10000 rpm (30 minutes). At the end of each centrifugation cycle, the supernatant is removed and the precipitated AuNRs re-dissolved in deionized water.

This protocol allowed preparation of AuNRs with absorption plasmon bands centered at 840 nm.

b) Microgel Derivatization Protocol with AuNRs

In a (2% by weight) solution of microgel particles synthesized according to Example 1 and prepared with acrylic acid, an AuNRs (1% by weight) solution was dispersed under continuous stirring for 1 hour. Microgels so prepared were characterized by electron transmission microscopy (data not shown).

Example 5

Optical Fiber (Tip and/or Lateral Surface) Functionalization Protocol with Silane Coupling Agents The silane functionalization protocol first envisaged the activation of silicon oxide (material forming some types of optical fibers) in a 5% nitric acid solution for 120 minutes at 90° C. Subsequently, the fiber was washed with water and allowed to react for 60 minutes in a hydrochloric acid solution (12 M HCl) at room temperature. The fiber is then allowed to dry in a stove at 75° C. for one hour.

Upon completion of this first activation step, silanization was carried out using a reactive silane solution (for example, γ-glycidoxypropyltrimethoxysilane, γ-aminopropyltriethoxysilane, γ-mercaptopropyltrimethoxysilane) in (10% w/w) ethanol. The fiber was left in immersion for 60 minutes; then it was washed with water, ethanol and dried under a flow of nitrogen.

Depending on the type of silane used, optical fibers with amino groups (where γ-aminopropyl-triethoxysilane is used) or epoxy groups (when γ-glycidoxypropyltrimethoxysilane is used) present on the surface were obtained.

Example 6

Functionalization Protocol with Thiols of Optical Fibers Having Gold Surfaces (Tips)

The self-assembled monolayer approach was used to functionalize the gold surface of the fibers with a layer of thiols. This protocol included a pretreatment with piranha solution (sulfuric acid and hydrogen peroxide, 3:1) to remove contaminants present thereon. After 1-2 minutes of immersion, the fiber was washed with distilled water and then immersed in a 10 mmol/L 11-mercapto-1-undecanoic acid or 16-mercapto-1-hexadecanoic acid type thiol solution for 30 minutes-24 hours.

Subsequently, the fiber was washed with ethanol, water and dried under a nitrogen flow.

Example 7

Binding Microgel Particles to the Surface of Silanized Fibers 7.1) Direct Approach Via Carbodiimide Microgel particles prepared according to Example 1 and including carboxylic groups (derived from acrylic acid) were covalently bound to the surface of the optical fiber functionalized with aminopropyltriethoxysilane (according to the procedure described in Example 5). The protocol included immersion of the optical fiber in a (5% w/v) microgel solution in the presence of 1-ethyl-3-methyl-(3-dimethylaminopropyl) carbodiimide (EDC, 500 mM) in a pH 4.5 buffer at 4° C. After 8 hour reaction time, the fiber was immersed (5 times) in deionized water solutions to remove excess reagents. Finally, the fiber was dried under a nitrogen flow. The microgel distribution on the surface of the optical fiber was observed and characterized by atomic force microscopy (data not shown).

7.2) Photo-Polymerization Approach

Microgels prepared according to Example 1 and containing amino groups were covalently anchored to the surface of the optical fiber by a multistep procedure.

A first fiber activation step provided for immersion of the optical fiber (previously functionalized with γ-aminopropyltrimethoxysilane according to the procedure described in Example 5) in a (10% w/v) aminobenzophenone solution in tetrahydrofuran (THF) at 65° C. for 4 hours. After the conjugation with aminobenzophenone, the fiber was washed with THF, ethanol and dried under a nitrogen flow.

The fiber so functionalized was then immersed in a (5% w/w) microgel solution for 2 hours and then dried under a nitrogen flow. The so deposited fiber was illuminated with a (100 W) UV lamp for 30 minutes for the covalent attack of the microgels on its surface. In fact, due to UV excitement, the benzophenone molecules give rise to radicals that are able to extract a proton from the nearby polymeric chains of the microgels and thus form a carbon-carbon bond.

After UV lamp lighting, the fiber was immersed (5 times) in deionized water solutions, dried under a nitrogen flow. The microgel distribution on the surface of the optical fiber was observed and characterized by atomic force microscopy (data not shown).

7.3) Pre-Activated Cross-Linker Approach

Microgel particles prepared according to Example 1 and including carboxylic groups (derived from acrylic acid) were covalently bound to the optical fibers surfaces functionalized with γ-mercaptopropyltrimethoxysilane (according to the procedure described in Example 5).

For the first step of the coupling process, a microgel solution containing carboxylic groups was suspended in a MES buffer with pH 5.0 at room temperature. After 2 hours, 2 mL of a solution containing 1-ethyl-3-methyl-(3-dimethylaminopropyl) carbodiimide (EDC, 250 mM) and N-hydroxy-sulfosuccinimide (500 mM, NHS) were added. The activation reaction of the carboxylic groups was left under stirring for 30 minutes and then 2 mL of maleimido caproic acid N-ε-hydrazide (EMCH) were added. The solution was kept under stirring for 2.5 hours to allow coupling reaction between the activated carboxylic groups present in the microgels and hydrazide in the EMCH. In order to remove unreacted material, the microgels were centrifuged and resuspended in a 25 mM HEPES buffer with pH 7.

For the fiber-conjugation step, the optical fiber (previously functionalized with γ-mercaptopropyltrimethoxysilane) was immersed in a (5% w/v) microgel solution in a 25 mM HEPES buffer with pH 7. After 8 hour reaction time, the fibers were immersed 5 times in deionized water solutions to remove excess reagents. Finally, the fiber was dried under a nitrogen flow and the distribution of the microgels on the surface of the optical fiber was observed and characterized by atomic force microscopy.

Example 8

8.1) Encapsulation Protocol for Bioactive Molecules (in Solution)

1 mg of lyophilized microgels of Example 4 were dispersed in 1 mL of a $10^{-4}$ M solution of doxorubicin in 0.01 M saline buffer (PBS) with pH 7.4. The solution was allowed to equilibrate for 12 hours on a rotating plate at room temperature. The supernatant solution was separated from the microgels by ultracentrifugation at room temperature (in a controlled temperature centrifuge).

The supernatant solution was recovered and analyzed by UV/VIS spectrophotometry. Absorbance readings were obtained at 464 nm (maximum absorption of doxorubicin). Doxorubicin concentrations in the supernatant solution were calculated based on calibration curves obtained from doxorubicin solutions with known concentrations in PBS at pH 7.4.

8.2) Encapsulation Protocol for Bioactive Molecules on Fiber

The optical fiber prepared according to Example 7.1 was immersed in 1 mL of a $10^{-4}$ M solution of doxorubicin in 0.01 M saline buffer (PBS) with pH 7.4. The solution was allowed to equilibrate for 12 hours at room temperature. Subsequently, the optical fiber was removed from the solution, which was recovered and analyzed by UV/VIS spectrophotometry. Absorbance readings were obtained at 464 nm (maximum absorption of doxorubicin). Doxorubicin concentrations in the supernatant solution were calculated based on calibration curves obtained from doxorubicin solutions with known concentrations in PBS at pH 7.4.

Example 9

9.1 Device for the Release of Doxorubicin.

The setup of this device provided firstly the optimization of the synthesis of thermoresponsive microgels and their derivatization with AUNRs in solution, followed by subsequent transfer to the optical fiber. The interaction between light emitted by the optical fiber and the AuNRs resulted in photothermal heating effects of the gel, followed by microgel compression processes (decrease in size) and ejection (thus release) of the doxorubicin trapped therein.

9.1.a. Synthesis of Microgel in Solution by Precipitation Polymerization

The microgel synthesis by precipitation polymerization was carried out using an aqueous solution (100 mL) containing a monomeric mixture of $4.2 \times 10^{-3}$ moles N-isopropylacrylamide (NIPAM), $4.2 \times 10^{-4}$ moles maleic acid (MA) and $3.4 \times 10^{-4}$ moles ethylene dimethacrylate. The mixture was degassed with nitrogen and heated to 70° C. Ammonium persulphate ($2.2 \times 10^{-4}$ moles) was added as initiator and the mixture was left under stirring at 70° C. for 4 hours. The microgels thus obtained were purified by the excess of unreacted monomers by dialysis (cut off membrane: 10000-14000 Dalton).

9.1.b. Synthesis of Gold Nanorods (AuNRs)

The synthesis of AuNRs involves the use of a protocol known as the "seed-mediated growth method". The procedure consists in preparing nucleation "seeds" by reducing a small amount of tetrachloroauric acid ($HAuCl_4$, 0.12 mL, 5 mM) in aqueous solution and in the presence of a hexadecyltrimethylammonium surfactant (CTAB, 2.5 mL mL, 0.2M) with a strong reducing agent, such as sodium borohydride ($NaBH_4$, 0.5 mL, 10 mM).

A small amount of these "seeds" (1 ml) was then introduced into the actual growth solution containing 25 mL of a 0.2 M solution of CTAB and 25 ml of a 0.2 M solution of benzyl dimethyl hexadecylammonium chloride. 5 mL of an aqueous solution of $HAuCl_4$ (5 mM), silver nitrate ($AgNO_3$, 2.8 mL, 4 mM) and 40 mL of water are added to this solution. After adding 1 ml of an aqueous solution of 0.8 M ascorbic acid, the dark yellow solution becomes colorless. NRs are purified by three centrifugation cycles at 10000 rpm (30 minutes). At the end of each centrifugation cycle, the supernatant is removed and the precipitated AuNRs re-dissolved in deionized water. This protocol allowed preparation of AuNRs with absorption plasmon bands centered at 840 nm.

9.1.c. Microgel Derivatization Protocol with AuNRs

An AuNRs (1% by weight) solution was dispersed under continuous stirring for 1 hour in a microgel (2% by weight) solution prepared with maleic acid.

Characterization of Properties of Microgel in Solution.

The hydrodynamic radius of the microgels depending on the temperature was determined by dynamic light scattering in different buffers (pH 3, pH7.5). The hydrodynamic radius was 400 nm at pH 7.5. Functional groups on the surface of the particles were determined quantitatively by potentiometric titration.

Microgels derivatized with AuNRs were characterized by electronic transmission microscopy. Changes in the size of the microgels derivatized with AuNRs at the AuNR absorbance wavelength (810 nm) were measured by dispersing a 1% microgel solution in PBS buffer with pH 7.4 at 36° C. and then irradiating at 810 nm (Laser/pulse surgical CW, 1.5 W power). The temperature of the solution was monitored by a thermocouple probe placed inside the test tube.

9.1.d. Encapsulation Protocol for Bioactive Molecules (in Solution)

1 mg of microgels derivatized with AuNRs were dispersed in 1 mL of a $10^{-4}$ M solution of doxorubicin in 0.01 M saline buffer (PBS) at pH 7.4. The solution was allowed to equilibrate for 12 hours on a rotating plate at room temperature. The supernatant solution was separated from the microgels by ultracentrifugation at room temperature (in a controlled temperature centrifuge).

The supernatant solution was recovered and analyzed by UV/VIS spectrophotometry. Absorbance readings were obtained at 464 nm (maximum absorption of doxorubicin). Doxorubicin concentrations in the supernatant solution were calculated based on calibration curves obtained from doxorubicin solutions with known concentrations in PBS at pH 7.4.

9.1.e Optical Fiber Functionalization Protocol (with Silane Coupling Agents)

The optical fiber functionalization was performed by activating the silicon oxide (material constituting some types of optical fibers) in a 5% nitric acid solution for 120 minutes at 90° C. Subsequently, the fiber was washed with water and allowed to react for 60 minutes in a hydrochloric acid solution (12 M HCl) at room temperature. The fiber was then dried in a stove at 75° C. for one hour.

Upon completion of this first activation step, silanization is carried out using a (10% w/v) solution of aminopropyltriethoxysilane in ethanol. The fiber was left in immersion for 60 minutes at 75° C.; then it was washed with water, ethanol and dried under a flow of nitrogen and finally in a stove at 50° C. overnight.

9.1.f. Microgel Covalent Anchoring to the Surface of Silanized Fibers

The microgels including the carboxylic groups (derived from maleic acid) were covalently bonded to the surface of the optical fiber functionalized with aminopropyltriethoxysilane. The optical fiber was immersed in a (5% weight/volume) microgel solution in the presence of 1-ethyl-3-methyl-(3-dimethylaminopropyl) carbodiimide (EDC, 500 mM) in a pH 4.5 buffer at 4° C. After an 8 hour reaction time, the fiber was immersed (5 times) in deionized water solutions to remove excess reagents. Finally, the fiber was dried under a nitrogen flow and the distribution of the microgels on the surface of the optical fiber was observed and characterized by atomic force microscopy (data not shown).

9.1.g. Fiber Anchored Microgel Derivatization Protocol with AuNRs and Encapsulation of Doxorubicin The derivatized optical fiber with the microgels was immersed in an AuNRs (1% by weight) solution under continuous stirring for 1 hour.

For the doxorubicin loading process, the optical fiber was immersed in 1 mL of a $10^{-4}$ M solution of doxorubicin in 0.01 M saline buffer (PBS) with pH 7.4. The solution was allowed to equilibrate for 12 hours at room temperature.

The supernatant solution was recovered and analyzed by UV/VIS spectrophotometry. Absorbance readings were obtained at 464 nm (maximum absorption of doxorubicin). Doxorubicin concentrations in the supernatant solution were calculated based on calibration curves obtained from doxorubicin solutions with known concentrations in PBS at pH 7.4.

9.1.h. Characterization of Doxorubicin Release by Optical Fiber Device

The release of doxorubicin microgels anchored to the fiber and derivatized with AuNRs was measured by immersing the fiber in PBS buffer with pH 7.4 at 36° C. and then irradiating at 840 nm (laser/pulse CW, 1.5 W power), corresponding to the absorption wavelength of AuNRs (840 nm). The temperature of the solution was monitored by a thermocouple probe placed inside the test tube. Buffer solution quantities were taken and concentrations of doxorubicin released in the solution were calculated by readings absorbance at 464 nm (maximum doses of doxorubicin absorption). A percentage of 80% of the amount of doxorubicin compared to the initial concentration being used was actually loaded within the microgels.

9.2. Device for the Release of Monoclonal Antibodies

The setup of this device provided firstly the synthesis in solution of microgels containing photosensitive molecules, such as nitrobenzyl cross-linkers, and with monoclonal antibodies with therapeutic activity loaded therein. The microgels were then transferred and bound to optical fiber. The interaction between light emitted from the optical fiber and the photosensitive cross-linker gave rise to photocleavage effects, responsible for the cleavage of chemical bonds in the polymer network, with consequent increase of the molecular mesh and release of monoclonal antibodies.

9.2.a. Multistep Synthesis of the Photosensitive Cross-Linker

Step a.1

The hydroxyethyl photolinker (Novabiochem®) photolabile precursor (0.01 moles) was suspended in anhydrous dichloromethane (1.4 moles) and the solution was kept under magnetic stirring in a nitrogen flow. Subsequently, this solution was allowed to cool to 0° C. and a solution of triethylamine (0.03 moles) and an acryloyl chloride solution (0.025 moles) in anhydrous dichloromethane was slowly added via a syringe. The reaction was allowed to proceed at room temperature under magnetic stirring for 12 hours. Subsequently, sodium bicarbonate (5% w/v aq.) diluted hydrochloric acid (1% v/v aq.) and deionized water were added to the reaction mixture. After evaporation of the solvent, the product was dissolved in a mixture of acetone:water (50:50). This mixture was left under stirring for one night at room temperature and filtered to remove any insoluble impurities and finally the acrylate monomer was extracted with dichloromethane. The product extracted into dichloromethane was washed sequentially with diluted hydrochloric acid (1% v/v Aq.) and deionized water, it was dried over magnesium sulphate and finally recovered after removal of the solvent.

Step a.2

The photosensitive acrylate monomer obtained from step a.1 (6 mmoles) was dissolved in N-methyl-2-pyrrolidone and left under magnetic stirring in an inert atmosphere. HBTU (6.5 mmoles), HOBt (6.5 mmoles) and N,N-diisopropylethylamine (11.8 mmoles) coupling agents were then added under stirring for 5 minutes and finally a derivative of the bi-functionalized polyethylene glycol (acrylate-PEG-amino) (0.6 mmol) in N-methyl-2-pyrrolidone. The reaction was allowed to proceed for one night, the product was precipitated in diethyl ether at 0° C. and centrifuged, the precipitate product was washed with ether and centrifuged twice. The reaction product (photocleavable cross-linker-(PC)) was subsequently left to dry under vacuum, re-dissolved in deionized water, and centrifuged to remove insoluble impurities. Finally, the product was left in dialysis (cut off 1000 dalton) and lyophilized.

9.2.b. Synthesis of Microgels in Solution by Emulsion Polymerization

Microgels for the release of monoclonal antibodies were synthesized by polymerization in an oil-in-water emulsion. 2-dimethylaminoethylmethacrylate (0.04 g), 2-aminoethylmethacrylate hydrochloride (0.01 g), PC cross-linker (0.0125 g in 200 mL dichloromethane) were added to 1 mL phosphate buffer (PBS) containing the Trastuzumab monoclonal antibody to be encapsulated. For studies about the release, the monoclonal antibody was also previously conjugated to a fluorescent dye, such as isothiocyanate fluorescein. Polyvinyl alcohol (Mw 530000) was used as a dispersing medium. The solution was sonicated for 2 minutes to obtain homogeneous dispersion and left 30 minutes in an inert atmosphere. Subsequently, ammonium persulfate (APS) (0.0005 g in 100 μL of water) and tetramethylethylenediamine (0.0001 g in 100 μL of water) were added to the reaction mixture by means of a syringe. The reaction was allowed to proceed under magnetic stirring for 2 hours at 4° C. The product was purified by dialysis (cut off membrane: 10000-14000 Dalton) in PBS at room temperature.

Characterization of Properties of Microgel in Solution and Release Studies.

The hydrodynamic radius of the microgels was determined by dynamic light scattering (using a Zetasizer Nano ZS (Malvern Instrument) and resulted in an average value of about 400 nm. For the release studies a 1 mg/mL solution of microgel was used with the encapsulated monoclonal antibody conjugated with fluorescein in PBS buffer with pH 7.4 at 36° C. This solution was irradiated at 400 nm (laser/pulse surgical CW, 1.5 W power) corresponding to the cross-linker activation wavelength. The temperature of the solution was monitored by a thermocouple probe placed inside the test tube.

After irradiation, the supernatant solution was separated from the microgels by ultracentrifugation at room temperature (in a controlled temperature centrifuge).

The supernatant solution was recovered and analyzed by spectrophotometry by performing fluorescence readings at 530 nm (fluorescein maximum emission) under excitation at 478 nm. Fluorescein conjugated antibody concentrations in the supernatant solution were calculated based on calibration curves obtained from fluorescein conjugated antibody solutions with known concentrations in PBS at pH 7.4. A percentage of 70% of the amount of antibody compared to the initial concentration being used was actually released from the inside of the microgels following irradiation with 400 nm light.

9.2.c Optical Fiber Functionalization Protocol with Silane Coupling Agents

The optical fiber functionalization protocol first envisaged activation of the silicon oxide (material constituting some types of optical fibers) in a 5% nitric acid solution for 120 minutes at 90° C. Subsequently, the fiber was washed with water and allowed to react for 60 minutes in a hydrochloric acid solution (12 M HCl) at room temperature. The fiber is then allowed to dry in a stove at 75° C. for one hour.

Upon completion of this first activation step, silanization was carried out using a solution of γ-glycidoxypropyltrimethoxysilane in sodium acetate buffer with pH 5 (10% w/w). The fiber was left in immersion for 60 minutes at 75° C.; then it was washed with water, ethanol and dried under a flow of nitrogen and finally in a stove at 50° C. overnight.

9.2.d. Microgel Covalent Anchoring to the Surface of Silanized Fibers

The microgels including the carboxylic groups (derived from 2-aminoethylmethacrylate hydrochloride) were covalently bonded to the surface of the optical fiber functionalized with γ-glycidoxypropyltrimethoxysilane. The protocol included immersion of the optical fiber in a microgel (5% weight/volume) solution in phosphate buffer at pH 8. After an 8 hour reaction time, the fiber was immersed (for 8 hours) in deionized water solutions to remove excess reagents. Finally, the fiber was dried under a nitrogen flow and the distribution of the microgels on the surface of the optical fiber was observed and characterized by atomic force microscopy (data not shown).

Characterization of the Release of Monoclonal Antibodies by Means of Optical Fiber Device The release of monoclonal antibodies from microgels anchored to the fiber and derivatized with photoactivable crosslinkers was measured by immersing the fiber in PBS buffer with pH 7.4 at 36° C. and then irradiated at 400 nm (laser/pulse CW, 1.5 W power) i.e a wavelength corresponding to the cross-linker activation wavelength. The temperature of the solution was monitored by a thermocouple probe placed inside the test tube. Quantities of the buffer solution were taken and the quantities of marked monoclonal antibody released by the fiber in the solution, following excitation at 478 nm, were determined by fluorescence readings at 530 nm for different irradiation/activation times. A percentage of 90% of the amount of antibody was actually released, with reference to the initial concentration loaded within the microgels.

The invention claimed is:

1. An optical fiber functionalized with at least one particle of a polymeric gel comprising at least one photosensitive molecule and at least one biomolecule,
   wherein the at least one particle of the polymeric gel is covalently bound to said optical fiber, and wherein the at least one particle of the polymeric gel has a hydrodynamic radius in the range of 0.01 to 5 μm.

2. The optical fiber according to claim 1, wherein the at least one particle of the polymeric gel is covalently bound on at least a part of its outer surface by a covalent bond selected from a group consisting of an amide bond, an ester, ether and thioether bond, a carbon-carbon, carbon-nitrogen, carbon-sulphur, carbon-phosphorus, carbon-oxygen, carbon-silicon bond.

3. The optical fiber according to claim 1, wherein the at least one particle of the polymeric gel has a hydrodynamic radius in the range of 0.1 to 2.5 μm and the polymeric gel is a microgel.

4. The optical fiber according to claim 1, wherein the at least one particle of the polymeric gel has a hydrodynamic radius in the range of 0.010 to 0.050 μm and the polymeric gel is a nanogel.

5. The optical fiber according to claim 1, wherein the at least one particle of polymeric gel is obtained from polymerization of one or more monomers selected from a group consisting of: acrylic monomers, vinyl monomers, stimulus-responsive monomers and bionert monomers.

6. The optical fiber according to claim 5, wherein said acrylic monomers are functionalized with carboxyl and/or amino functional groups, preferably selected from a group consisting of acrylic acid, methacrylic acid, fumaric acid, maleic acid, butylmethylacrylate (nBuMA), dimethylaminoethyl acrylate (DMAEA), acrylamide (AAm), aminoethyllmethacrylate (Aema), dimethylaminoethyl (meth) acrylate (DMAEMA), N-(3-aminopropyl) methacrylamide (APMA), or polyethylenimine (PEI).

7. The optical fiber according to claim 5, wherein said bionert monomers are selected from a group consisting of monomers derived from ethylene glycol, preferably polyethylene glycol acrylates, polyethylene glycol methacrylates, polyethylene glycol functionalized with acrylamides, methacrylamide functionalized polyethylene glycol, oligo (ethylene glycol)acrylate (OEGA), oligo(ethylene glycol) methacrylate (OEGMA), oligo(ethylene glycol)diacrylate (OEGDA), N-alkylacrylamide, vinylcaprolactone (VCL), and hydroxy-ethyl methacrylate.

8. The optical fiber according to claim 5, wherein said stimulus-responsive monomers include (N-isopropylacrylamide) and aminoethyl-methacrylate derivatives.

9. The optical fiber according to claim 1, wherein said at least one photosensitive molecule is selected from a group consisting of:
   azobenzene or its derivatives,
   a nitrobenzyl derivative,
   a fluorophore, preferably derived from malachite and carbocyanines,
   a particle of gold and/or silver; and
   a high refractive index particle.

10. The optical fiber according to claim 1, wherein the at least one biomolecule is selected from the group consisting of growth factors, neuroprotective molecules, molecules active for regeneration of the central nervous system, drugs and prodrugs and combination thereof, antineoplastic agents, biological response modifiers, hormones, vitamins, peptides, enzymes, antiviral agents, radioactive compound, monoclonal antibodies, genetic material, and cells.

11. The optical fiber according to claim 1, wherein said optical fiber comprises a cladding having a cylindrical side surface which defines a longitudinal axis, and a tip formed by a transverse surface extending crosswise with respect to said longitudinal axis, wherein said particles are covalently bound to the tip and/or the cladding.

12. A device for releasing at least one biomolecule in a human or animal tissue or compartment, the device comprising:
   at least one optical fiber according to claim 1, wherein said photosensitive molecule is adapted to be activated in a predetermined range of wavelengths;
   a lighting system configured to generate a light beam that propagates from inside the optical fiber to the outside, wherein said light beam has a wavelength comprised in said predetermined wavelengths range,
   an optical connector that connects the optical fiber to the lighting system.

* * * * *